United States Patent [19]

Bravo et al.

[11] Patent Number: 4,940,839
[45] Date of Patent: Jul. 10, 1990

[54] METHOD OF TOMATO PROTOPLAST FUSION AND REGENERATION OF HYBRID PLANTS THEREFROM

[75] Inventors: Janis E. Bravo; David A. Evans, both of Palmyra, N.J.

[73] Assignee: DNA Plant Technology Corporation, Cinnaminson, N.J.

[21] Appl. No.: 914,130

[22] Filed: Oct. 1, 1986

[51] Int. Cl.$^5$ .................... A01H 1/04; C12N 15/00; C12N 5/00; C12N 5/02
[52] U.S. Cl. ................ 800/220; 435/172.2; 435/240.47; 435/240.51; 435/240.54; 800/DIG. 44; 800/DIG. 71
[58] Field of Search .............. 435/240, 241, 172.2, 435/240.47, 240.51, 240.54; 800/1

[56] References Cited

PUBLICATIONS

Biological Abstracts vol. 83 (1987), 86058.
Biological Abstracts 32101664.
Chemical Abstracts vol. 105 (1986) No. 39528q.
Handley et al. 1986, Theor. Appl. Genet. 71:691–697.
Handley et al. 1985, Plant Sci. 42:201–207.
Taylor et al. 1982, Theor. Appl. Genet. 61:59–63.
O'Connell et al. 1985, Biol. Abstr. 80:#39952.
Niedz et al. 1985, Plant Science 39:199–204.
Zapata et al. 1977, Plant Sci. Lett. 8:119–124.
Shepard et al. 1983, Science 219:683–688.
Adams et al. 1985, Plant Science 40:209–219.

Primary Examiner—Charles F. Warren
Assistant Examiner—David T. Fox
Attorney, Agent, or Firm—Pennie & Edmonds

[57] ABSTRACT

The present invention relates to a method of producing a hybrid plant of a wild species and a cultivated species of Lycopersicon which comprises fusing protoplasts of the wild and cultivated species and recovering a hybrid plant from fused protoplasts under selective regeneration conditions wherein the wild species is incapable of regeneration under said conditions.

14 Claims, 1 Drawing Sheet

METHOD OF TOMATO PROTOPLAST FUSION AND REGENERATION OF HYBRID PLANTS THEREFROM

FIELD OF THE INVENTION

The present invention relates to a method of producing somatic hybrids and cybrids of commercial tomato varieties.

BACKGROUND OF THE INVENTION

The process of introducing desirable wild-type traits, such as disease resistance, plant habit and the like, into cultivated varieties has long been a basis for improving crop plants. Sexual hybridization is the traditional method used in crop improvement, but its use may be limited because of the natural barriers to hybridization which frequently exist in cultivated species. This particular effort has been severely restricted in the cultivated tomato *Lycopersicon esculentum*, because the opportunity for gene flow between the cultivated variety and its wild relatives is so curtailed by interspecific incompatabilities. Alternative methods to traditional breeding schemes, such as protoplast fusion and regeneration, have also been intensely investigated in tomato; however, these techniques as applied have had very limited success since the tomato, especially the cultivated variety, is much more resistant to regeneration from protoplasts than are other solanaceous species such as tobacco or potato.

In an attempt to overcome the difficulty of regenerating tomato, those interested in producing somatic hybrids of tomato have fused tomato protoplasts with protoplasts of certain species of the genus Solanum, which is more commonly easily regenerable. Although this technique frequently does allow the regeneration of protoplast fusion derived plants, a disadvantage arises in that the regeneration does require the expression of genes from Solanum. Since evidence suggests that genes controlling regeneration are polygenic and unlinked, all previous selection systems have produced regenerated plants which would necessarily have a minimum of several Solanum chromosomes.

Because previous systems have generally relied on Solanum species for regeneration, the known reports of somatic hybridization have nearly all been between two distinct genera, Lycopersicon and Solanum. As might be expected, however, because of the taxonomic distance between the fusion partners, the resultant plants are almost always completely infertile. For example, Melchers, et al. (*Carlsberg Res. Commun.* 43: 203–18, 1978) described fusion products between *L. esculentum* and the potato, *S. tuberosum;* however, all resulting plants were completely sterile and therefore not useful in a breeding program. This result was later confirmed by Shepard, et al. (Science 219: 683–688, 1983). Similarly, Jain, et al. (Abst. First Int. Cong. Plant . Mol. Biol., p.61, 1985) in fusing protoplasts of *L. esculentum* and *S. nigrum* recovered a number of somatic hybrids, but none of the regenerated plants were fertile.

In an attempt to use Solanum-Lycopersicon hybrids as breeding material, Handley, et al. *Theoret. Appl. Genet.* 71: 691–697, 1986) devised a method of protoplast fusion between *Solanum lycopersicoides* and *Lycopersicon esculentum*, in which the selection for hybrids at least nominally favored the *L. esculentum* parent. However, although in principle the tomato was favored, the selection step which relies on speed of regeneration actually favors *S. lycopersicoides*, which grows faster than *L. esculentum*. Therefore, ultimately, the Handley method uses a medium which in fact favors Solanum over Lycopersicon.

An attempt has also been made to fuse *L. esculentum* with the more closely related wild species, *L. pennellii* (M. O'Connell, et al., *Theoret. Appl. Genet.* 70: 1–12, 1985). Although the sexual hybrid of these two species grows well in culture and is readily regenerable from protoplasts, the somatic hybrids produced only callus with no hybrid plants ultimately produced.

The present invention, on the other hand, relates to a method of producing tomato somatic hybrids and cybrids in which the foregoing problems are eliminated. As used throughout the specification and claims, the term "hybrid" is intended to encompass both somatic hybrids and cybrids. The method utilizes a medium which truly selects for *L. esculentum* so that only unfused *L. esculentum* cells, *L. esculentum* cybrids with *L. esculentum* nuclear genes, and somatic hybrids between *L. esculentum* and related wild species are regenerated. Thus, the present method is more likely to ultimately yield gene combinations which contain a full tomato genome than previous methods have been.

BRIEF DESCRIPTION OF THE INVENTION

The present invention relates to a method of producing a hybrid plant of a wild species and a cultivated species of Lycopersicon which comprises fusing protoplasts of the wild and cultivated species and recovering a hybrid plant from fused protoplasts under selective regeneration conditions wherein the wild species is incapable of regeneration under said conditions.

DETAILED DESCRIPTION OF THE INVENTION

Figure 1:
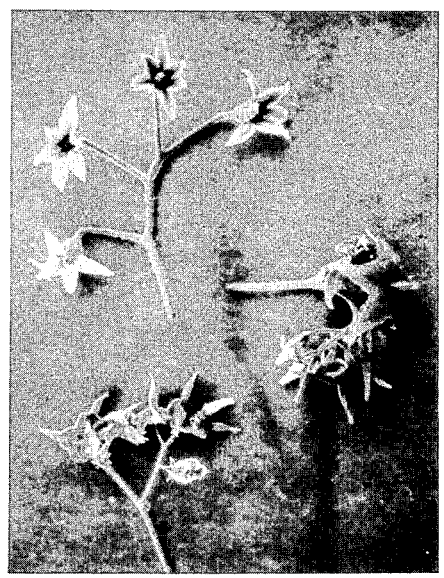
FIG. 1 is a photograph showing floral inflorescences of an *L. esculentum—L. peruvianum* hybrid (top); cultivated tomato, *L. esculentum* (four-flowered plant); and the wild species *L. peruvianum* (nine-flowered plant).

The present method relies on a selective system of regeneration of fused protoplasts wherein the culture medium composition is such that the wild species is incapable of being regenerated on it. An additional, although optional, feature of the method is that polyethylene glycol (PEG) is used in the fusion medium. The use of PEG in protoplast fusion is, of course, quite common; however, in the present method, *L. esculentum* is sensitive to PEG treatment. Many *L. esculentum* cells die in the fusion procedure so that there is a cell selection against unfused L. esculentum; thus, those cells which survive and ultimately produce plants are most likely to be either *L. esculentum* cybrids with an *L. esculentum* nucleus or the wild species with *L. esculentum* somatic hybrids. Therefore, the method effectively guarantees that the possible undesired plant types will most likely not regenerate, and the majority of plants which do regenerate will be the desired hybrid types.

The method does not, as noted above, rely on the wild species for regeneration; thus, overall, the spectrum of regenerated plants is highly favorable to the expression of tomato genes, and in particular, expression of a full tomato genome is more probable. On the other hand, because the regeneration is based on cultivated tomato, the procedure is readily applicable to other wild species, whereas a wild-species based regeneration system would have to be varied depending on each of the different wild species used.

The method used for protoplast fusion does not differ substantially from the techniques generally practiced in the art. In general terms, protoplasts are obtained by excision of plant tissue and enzymatic treatment of the tissue to remove the cell walls. Some commonly used enzymes include cellulases, hemicellulases and pectinases. Although the enzyme or enzymes used will vary depending on the plant tissue being used, it is within the knowledge of the skilled artisan to determine which treatment is most appropriate for the purpose. A number of different tissue types may be used to produce protoplasts from cultivated tomato, but the preferred tissue for the present method is leaf mesophyll.

Rarely, isolated protoplasts will fuse spontaneously. It is more often the case that chemical treatment is required to induce the desired levels of protoplast fusion. A number of different chemicals such as polyvinyl alcohol or various PEG derivatives may be suitable for this purpose. However, as already noted, it is preferred that PEG be used since this provides an initial selection against any unfused cells of the cultivated species in the fusion medium, thereby substantially preventing future regeneration of non-hybrid *L. esculentum* plants. Addition of PEG will cause agglutination of the protoplasts, which then fuse during elution in the presence of calcium and high pH, preferably at least pH 10. The preferred molecular weight of the PEG is about 1540, but this may be varied within a broad range The specific compositions and procedures involved in protoplast fusion are well known in the art and need not be elaborated further here.

Following protoplast fusion, the viable cells remaining in the fusion medium are somatic hybrids, cybrids having either *L. esculentum* or wild-type nucleus and unfused wild type. These cells are then transferred to a regeneration medium which favors the regeneration of the cultivated species, while substantially preventing the regeneration of the wild type species.

The initial culturing step utilizes a medium modified from Murashige and Skoog (*Physiol. Plant* 15: 473–497, 1962), containing mannitol as osmoticum, generally in an amount of about 0.3M, as well as containing one or more sugars, selected from sucrose, glucose and sorbitol, in a combined amount of about 0.1M. This medium is supplemented with hormones, including an auxin and a cytokinin in a respective ratio of about 2:1. Although any auxin and cytokinin may be employed, NAA as auxin and zeatin riboside as cytokinin are particularly effective in amounts of about 1–2 mg/1 and 0.5–1 mg/1, respectively. This medium permits cell wall formation, usually within a period of about 1–2 days. After cell wall formation, the same medium, containing 0.2M mannitol is added; in this phase, cell division begins. Cells of the wild species do not even reach the stage of cell division in these media, and therefore, colony formation cannot occur, and no adult wild species plants will be produced.

Following the initiation of regeneration of the fused protoplasts in which the cultivated species predominates dividing cells are cultured on a medium which promotes colony formation. At this stage the wild species has been substantially eliminated; therefore, screening is no longer necessary, and any medium which will support tomato protoplast colony formation is acceptable. A particularly successful medium is the same modified MS medium, containing 0.17M mannitol, 0.03M sucrose, an auxin and a cytokinin, preferably 2,4-D and 6-BA. Similarly, shoot regeneration may be accomplished by any means known to induce shoot production in tomato; success in regenerating adult plants has been achieved by transferring visible colonies to a solidified MS medium containing 0.08M mannitol, 0.03 sucrose, a cytokinin and a gibberellin, preferably zeatin riboside and $GA_3$.

The present method may readily be applied to protoplast fusion between the cultivated tomato species *L. esculentum* and any closely related wild type species. This includes both species of the same genus, Lycopersicon, as well as species of the genus Solanum.

Particular success with this method has been achieved with the use of an *L. esculentum* - *L. peruvianum* pairing, and this is a preferred combination.

The method of the present invention will be better understood by reference to the following non-limiting examples.

EXAMPLE 1

The following example shows the method of protoplast isolation.

ISOLATION OF TOMATO PROTOPLASTS

Cultivated tomato L. esculentum donor plants are grown in an environmental growth chamber (16-hour day, 25° C., 4,000 lux) for 12–15 days until first leaves are fully expanded.

Leaves are sterilized in 10-percent Clorox for 8 minutes and are then rinsed twice in sterile deionized water.

Lower epidermis is removed from the leaves with fine jewelers forceps. Leaves are placed peeled side down in enzyme solution containing 0.4M mannitol, 220 mg/1 $CaCl_2 2H_2O$, 750 mg/1 $KNO_3$, 0.1% Driselase, 0.2% Cellulysin, 0.2% Macerase at pH 5.6.

Protoplasts are fully digested after three hours in the enzyme solution.

WILD SPECIES OF TOMATO

Cell suspension cultures are maintained on Murashige-Skoog liquid medium containing 2 mg/1 2,4-D. Culture are maintained on a 4-day subculture interval and are subcultured 2 days before protoplast isolations are attempted.

Cells (2 ml) are centrifuged for 4 minutes at 100 xg. Culture media is removed and replaced with enzyme solution (same as above except enzymes are 1.5% Cellulase RS, 0.4% Pectolyase Y23, 0.3% Macerase, 0.15% Driselase). Protoplasts are fully digested in 5 hours.

PURIFICATION

Crude protoplast mixture is centrifuged twice at 100 xg for 4 minutes, once to remove the enzyme and once to rinse. Then protoplasts are suspended in rinse solution containing 21% sucrose. Centrifugation is performed again for 8 minutes at 100 xg. Purified protoplasts float and are collected before mixing for fusion.

EXAMPLE 2

The basic fusion procedure is performed in accordance with the techniques described by Kao and Michayluk, Planta 115: 355–367, 1974. A list of the solutions necessary for the procedure and their composition is shown in Table 1. The isolated leaf mesophyll protoplasts of *L. esculentum* are washed with enzyme washing solution and allowed to sit for one hour. Protoplasts of *L. peruvianum* in cell suspension are also washed, and immediately used in the fusion procedure. Protoplasts are mixed in a 2:1 ratio (cell suspension: leaf mesophyll); about .15ml of the mixture is pipetted onto a sterile glass cover slip and allowed to settle for about 5 minutes, before the addition of about 0.45 ml of PEG solution (MW=1540). The PEG treatment is continued from 5-15 minutes at room temperature. PEG-eluting solution is then added over a 20 minute period. The protoplasts are then washed four times with culture medium before incubation.

TABLE 1

| Solutions Necessary for Protoplast Fusion | |
|---|---|
| PEG Fusing Solution Dissolve: | 0.3 M mannitol |
| | 10 mM $CaCl_2.2H_2O$ |
| | 0.7 mM $KH_2PO_4$ |
| in 50 ml final volume. | |
| To this 50 ml, add 25 g of PEG (1540) and dissolve | pH = 5.8 |
| PEG Eluting Solution Dissolve: | |
| (A) 100 mM glycine .4 M mannitol in 100 ml final volume. | (B) 100 mM $CaCl_2.2H_2O$ 0.4 M mannitol 10 ml DMSO in 100 ml final volume. pH = 10.5 using NaOH pellets. |

EXAMPLE 3

Protoplasts are cultured initially in a modified Murashige and Skoog (MS) medium containing 0.3M mannitol and 0.1M other sugars (sucrose, glucose and sorbitol) 1 mg/1 NAA, and 0.5 mg/1 zeatin riboside at 25° C. After cell wall formation, one half volume of the above medium, containing 0.2M mannitol is added. Colony development (32–64 cells) is achieved on the same basal medium containing 0.17M mannitol and 03 M sucrose, 0.2 mg/1 2,4-D and 0.5 mg/1 6-BA. Visible colonies are placed on solidified medium containing 0.08M mannitol, 0.03M sucose, 1.0 mg/1 zeatin riboside, and 0.2 mg/1 $GA_3$ to induce shoot regeneration. Cultures are gradually placed under conditions of 3600 lux light (16 hrs. light/8 hrs. dark).

The resulting hybrid plants have an intermediate leaf morphology between the two parents. The flower arrangement is like *L. peruvianum*, but flower size is larger than either parent. These plants are shown in FIG. 1. Pollen viability of the hybrid ranges from 2% to 80%. The cytoplasmic composition of the hybrid plants shows plants having esculentum chloroplasts and mitochondria, and plants having esculentum chloroplasts and peruvianum mitochondria. A summary of the results observed is shown in Table 1. The foregoing procedures were also successfully employed in producing hybrids between *L. esculentum* and the wild species *L. pennelli*.

TABLE 2

Analysis of tomato regenerants following fusion between *Lycopersicon esculentum* (L.e.) and *L. peruvianum* (L.p.)

| Explant No. | | Isozyme+ | Cp DNA | MtDNA | **P.V.(%) | cp/Guard Cell |
|---|---|---|---|---|---|---|
| Le + LP | 100 | Hyb. | L.e. | L.p. | 46.2 | 36.4 |
| | 101 | Hyb. | L.e. | | 34.0 | 38.4 |
| | 102 | Hyb. | L.e. | | 72.0 | 32.3 |
| | 103 | Hyb. | L.e. | L.p. | 69.0 | 32.6 |
| | 104 | L.e. | L.e. | | 98.0 | 11.4 |
| | 105 | L.e. | L.e. | | 96.0 | 8.0 |
| | 106 | L.e.(Aps-1) | L.e. | | | 14.9 |
| | 107 | Hyb. | L.e. | | 10.0 | 31.6 |
| | 108A | Hyb. | L.e. | | NFA | 25.6 |
| | 108B | Hyb. | L.e. | | 65.6. | 40.8 |
| | 109A | Hyb. | L.e. | | 30.3 | 34.2 |
| | 109B | Hyb. | L.e. | | 20.0 | 30.3 |
| | 109C | Hyb. | L.e. | | 53.0 | 28.5 |
| | 110A | Hyb. | L.e. | | 65.8 | 32.0 |
| | 110B | Hyb. | L.e. | | 61.9 | 32.2 |
| | 111A | Hyb. | L.e. | | 4.0 | 36.0 |
| | 111B | Hyb. | L.e. | | 2.0 | 12.0 |
| | 112 | Hyb. | L.e. | | 4.0 | 27.3 |
| | 115A | Hyb. | L.e. | | 76.5 | 33.5 |
| | 115B | Hyb. | L.e. | | 68.0 | 9.2 |
| | 0 | Hyb. | L.e. | | 65.9 | 39.8 |
| | 8A | Hyb.(GOT) | L.e. | | NFA | |
| | 8B | Hyb.(GOT) | L.e. | | 70.0 | 31.7 |
| Lp + Le | 50 | Hyb.(GOT) | | | 57.6 | |
| | −21 | Hyb. | L.e. | | 46.0 | |
| | −23 | Hyb. | L.e. | | 66.0 | |
| | −25 | Hyb. | L.e. | | NFA | |
| | −28 | Hyb.(GOT) | L.e. | | 10.0 | |
| | −29 | Hyb. | L.e. | | 85.0 | |
| | −40 | Hyb. | L.e. | | 79.0 | |
| | −42 | Hyb.(GOT) | L.e. | | 73.0 | |
| | −45 | Hyb. | L.e. | | 59.0 | |
| | −71 | Hyb. | | | NFA | |
| | −86 | Hyb. | | | 57.0 | |
| | −96 | L.e. | L.e. | | NFA | |

TABLE 2-continued

Analysis of tomato regenerants following fusion between
*Lycopersicon esculentum* (L.e.) and *L. peruvianum* (L.p.)

| Explant No. | Isozyme+ | Cp DNA | MtDNA | **P.V.(%) | cp/Guard Cell |
|---|---|---|---|---|---|
| −9 | Hyb.(GOT) | | | 66.0 | |

*NFA = no flowers yet available
+Unless otherwise indicated, nuclear identity of fusion products were determined using four different isozymes: Aps-1 is acid phosphatase-1, located on chromosome 6; GOT-3 is glutamate oxaloacetate transaminase, located on chromosome 7; Pgm-2 is phosphoglucomutase, located on chromosome 4; PRX-2 is peroxidase, located on chromosome 2.
**Pollen viability, determined by staining with acetocarmine

What is claimed is:

1. A method of producing a hybrid plant of a wild species of Lycopersicon and *Lycopersicon esculentum* which comprises fusing protoplasts of the wild and cultivated species and recovering hybrid plants capable of producing viable pollen from fused protoplasts under selective regeneration conditions, wherein the wild species is incapable of plant regeneration under said conditions.

2. The method of claim 1 wherein the wild species is *L. peruvianum* or *L. pennelli*.

3. The method of claim 1 wherein the protoplasts are fused in a polyethylene glycol fusion solution.

4. The method of claim 1 wherein the regeneration conditions comprise an initial step of culturing fused protoplasts in a modified MS medium comprising about 0.3M mannitol, about 0.1M other sugars or sugar alcohols, wherein the sugars or sugar alcohols are selected from the group consisting of sucrose, glucose and sorbitol; and an auxin, and a cytokinin in a molar ratio of about 2:1.

5. The method of claim 4 wherein the auxin is NAA, and the cytokinin is zeatin riboside.

6. The method of claim 4 wherein regeneration conditions comprise the further step of adding to said initial culture one half volume of a modified MS medium comprising about 0.2M mannitol.

7. The method of claim 6 wherein regeneration conditions comprise the further step of culturing cells on a medium which promotes colony formation.

8. The method of claim 7 wherein regeneration conditions comprise initiating colony formation in a modified MS medium comprising about 0.17M mannitol, about 0.03M sucrose, about 0.2 mg/l 2,4-D and about 0.5 mg/l 6-BA.

9. The method of claim 8 wherein regeneration conditions include the further step of culturing colonies on a medium which initiates shoot formation.

10. The method of claim 9 wherein regeneration conditions comprise initiating shoot formation by culturing colonies on a solid, modified MS medium comprising about 0.08M mannitol, about 0.03M sucrose, about 1 mg/l zeatin riboside and about 0.2 mg/l $GA_3$.

11. An adult hybrid plant produced by the method of claim 1.

12. The hybrid plant of claim 11 wherein the cultivated species is *L. esculentum* and the wild species is *L. peruvianum* or *L. pennelli*.

13. The hybrid plant of claim 12 which is a somatic hybrid.

14. The hybrid plant of claim 12 which is a cybrid.

* * * * *